US010390530B2

(12) United States Patent
Klostermann et al.

(10) Patent No.: US 10,390,530 B2
(45) Date of Patent: Aug. 27, 2019

(54) USE OF HYDROPHOBIC, SELF-EMULSIFYING POLYGLYCEROL ESTERS AS ADJUVANTS AND ANTI-SPRAY-DRIFT AGENTS

(71) Applicants: Michael Klostermann, Essen (DE); Joachim Venzmer, Essen (DE); Rene Haensel, Dorsten (DE); Ewald Sieverding, St. Johann (DE)

(72) Inventors: Michael Klostermann, Essen (DE); Joachim Venzmer, Essen (DE); Rene Haensel, Dorsten (DE); Ewald Sieverding, St. Johann (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/517,457

(22) PCT Filed: Oct. 1, 2015

(86) PCT No.: PCT/EP2015/072681
§ 371 (c)(1),
(2) Date: Apr. 6, 2017

(87) PCT Pub. No.: WO2016/055344
PCT Pub. Date: Apr. 14, 2016

(65) Prior Publication Data
US 2017/0295782 A1    Oct. 19, 2017

(30) Foreign Application Priority Data
Oct. 8, 2014   (EP) .................................... 14188067

(51) Int. Cl.
*A01N 25/30* (2006.01)
*A01N 25/06* (2006.01)
*A01N 25/04* (2006.01)

(52) U.S. Cl.
CPC ............. *A01N 25/30* (2013.01); *A01N 25/04* (2013.01); *A01N 25/06* (2013.01)

(58) Field of Classification Search
CPC ......... A01N 25/30; A01N 25/04; A01N 25/06
USPC ...................................... 514/210
See application file for complete search history.

(56) References Cited

U.S. PATENT DOCUMENTS

| 8,163,673 | B2 | 4/2012 | Giessler-Blank et al. |
| 8,344,089 | B2 | 1/2013 | Frey et al. |
| 9,126,163 | B2 | 9/2015 | Giessler-Blank et al. |
| 2007/0190096 | A1 | 8/2007 | Arimoto |
| 2008/0175930 | A1 | 7/2008 | Baseeth |
| 2009/0035400 | A1 | 2/2009 | Baseeth |
| 2009/0227459 | A1 | 9/2009 | Xu et al. |
| 2010/0113275 | A1 | 5/2010 | Qin et al. |
| 2011/0201504 | A1 | 8/2011 | Merlet |
| 2012/0046168 | A1 | 2/2012 | Pullen et al. |
| 2013/0150241 | A1 | 6/2013 | Elsik |
| 2015/0065346 | A1 | 3/2015 | Baseeth |

FOREIGN PATENT DOCUMENTS

| CN | 103442559 | 12/2013 |
| EP | 1 787 514 A1 | 5/2007 |
| EP | 2 181 594 A1 | 5/2010 |
| EP | 2 420 141 A1 | 2/2012 |
| WO | WO 2008/091871 A2 | 7/2008 |
| WO | WO 2009/111779 A1 | 9/2009 |
| WO | WO 2010/051435 A2 | 5/2010 |
| WO | WO 2012/145177 A1 | 10/2012 |
| WO | WO 2014/066466 | 5/2014 |

OTHER PUBLICATIONS

International Search Report dated Nov. 30, 2015, in PCT/EP2015/072681 filed Oct. 1, 2015.
U.S. Appl. No. 10/216,131, filed Aug. 9, 2002, US-2003-0118614-A1, Ewald Sieverding, et al.
U.S. Appl. No. 11/006,949, filed Dec. 8, 2004, US-2005-0130842-A1, Ingo Fleute-Schlachter, et al.
U.S. Appl. No. 11/685,438, filed Mar. 13, 2007, US-2007-0213226-A1, Ewald Sieverding, et al.
U.S. Appl. No. 15/103,015, filed Jun. 9, 2016, US-2016-0311961-A1, Michael Klostermann, et al.
Office Action issued May 14, 2019, in Taiwan Patent Application No. 104132845 filed Oct. 6, 2015.

*Primary Examiner* — Kristin A Vajda
(74) *Attorney, Agent, or Firm* — Oblon, McClelland, Maier & Neustadt, L.L.P.

(57) ABSTRACT

Compositions comprising at least one hydrophobic, at least partially water-insoluble polyglycerol ester in combination with at least one emulsifier, and the use thereof.

17 Claims, 1 Drawing Sheet

USE OF HYDROPHOBIC, SELF-EMULSIFYING POLYGLYCEROL ESTERS AS ADJUVANTS AND ANTI-SPRAY-DRIFT AGENTS

Compositions comprising at least one hydrophobic, at least partially water-insoluble polyglycerol ester in combination with at least one emulsifier, and the use thereof.

So-called adjuvants or else auxiliaries or additives are frequently employed in crop protection, in pesticides and also in the industrial non-crop field in order to improve the biological activity of such pesticides or pesticide mixtures. The activity is frequently also referred to as efficacy. The Pesticides Safety Directorate (PSD, executive arm of the Health and Safety Executive (HSE), a non-state, public organization in Great Britain) defines an adjuvant as a substance which, other than water, is not pesticidally active itself, but enhances the efficacy of a pesticide (http://www.pesticides.gov.uk/guidance/industries/pesticides/topics/pesticide-approvals/legislation/adjuvants-an-introduction). These substances are either added to the aqueous spray mixture shortly before application and spraying (as a tank mix additive) or else incorporated directly into crop protection agent formulations. In the context of the use of the word "adjuvant", patents or the literature frequently use, as synonyms, the terms "surfactant" or "wetting agent", which, however, are far too far-reaching and may be interpreted more as generic terms. Owing to the use intended here, recourse is made to the term "adjuvant".

In practice, there exists a large number of crop protectants which only attain an acceptable efficacy, in other words a practically relevant activity, with the aid of adjuvants. Here, the adjuvants aid in compensating for the weaknesses of the active substance, such as, for example, the UV sensitivity of avermectins (which are degraded by ultraviolet radiation) or the instability of sulphonyl ureas to exposure to water. As a rule, more recent active substances are not water-soluble, and, in order to be able to spread effectively on a target=target organism=plants, adjuvants are imperative for the aqueous spray mixture for compensating for the poor wetting of surfaces by means of physically influencing the aqueous solutions. Moreover, adjuvants help overcome technical application problems, such as low water application volumes, different water qualities and the trend towards increased application rates. Increasing the pesticidal activity and compensating for weaknesses of the crop protection agents by adjuvants is generally referred to as increasing the efficacy or enhancing the activity of the crop protection agent application.

Chemical or biological crop protection agents (hereinbelow also referred to as pesticides) or pesticide mixtures are being employed in crop protection, in pest control and in the industrial sector. Examples of these may be herbicides, fungicides, insecticides, growth regulators, molluscicides, bactericides, virucides, micronutrients and biological crop protection agents which are based on natural substances or on live or treated or processed microorganisms. Pesticidal active substances are listed together with their fields of application for example in 'The Pesticide Manual', 14$^{th}$ edition, 2006, The British Crop Protection Council; biological active substances can be found, for example, in 'The Manual of Biocontrol Agents', 2001, The British Crop Protection Council. In what follows, "pesticide" is always used as a collective term.

In practice, such crop protection agents are frequently added to a tank containing water and distributed in the so-called spray mixture with gentle stirring so as to dilute the concentrated formulation of the active substance before spraying and to make it compatible with the plants. In this context, adjuvants are either coformulated into the crop protection formulation before the tank mixing process or else admixed to the spray mixture as separate tank mix additives.

To cultivate agricultural areas, these spray mixtures are atomized above a field. In this context, atomizing means the formation of droplets by mechanical action on a liquid medium, preferably by rotating objects and/or by releasing (reducing) the pressure at small apertures, especially preferably spray generated with the aid of nozzles.

For the cultivation of agricultural areas, 100 to 1000 l of spray mixture are, as a rule, sprayed per hectare. In exceptional cases, however, these limits may vary greatly upwardly or downwardly. In so-called low-volume applications, for example, very low volumes of down to 1.5 l/ha are sprayed, while in the case of application using the so-called lance technique very high volumes of up to 15 000 l/ha may be reached. The atomization process may be effected in this context either from positions at great height, for example by spraying spray mixtures from an aircraft, or from positions close to the soil, for example by spraying spray mixtures by means of a spraying boom mounted on a tractor. Other equipment such as spray lances or knapsack sprayers are also known for the application of spray mixtures.

Frequently, synthetic surfactants such as, for example, ethoxylated alcohols or alkylpolyglycosides are employed as adjuvants. The use of water-soluble, hydrophilic polyglycerol esters as adjuvants in crop protection formulations is likewise known (WO 2002/034051, US 2006-0264330A1). As a rule, these adjuvants share the fact that they are water-soluble hydrophilic substances. Moreover, alkoxylated trisiloxane surfactants are frequently employed as adjuvants, and these reduce the static surface tension of spray mixtures or water significantly more than organic surfactants which have been used in the past, such as, for example, nonylphenol ethoxylates. Trisiloxane surfactants have the general structure $Me_3SiOSiMeROSiMe_3$, where the radical R represents a polyether radical. The use of super spreading trisiloxane surfactants, such as, for example, BREAK-THRU® S-240, Evonik Industries AG, in combination with a pesticide results in an improvement in the pesticide uptake by the plant and generally in an increase in its activity or efficacy. U.S. Pat. No. 6,734,141 describes that it is specifically a low surface tension and not necessarily the spreading which is responsible for this increase in efficacy. In the prior art, the term surface tension is understood as meaning the static surface tension. In the case of trisiloxanes, for example, the static surface tension is approximately 20 to 25 mN/m.

Many tank mix additives, specifically the abovementioned ethoxylates or alkyl polyglycosides, will, when stirred in, cause great foaming of the spray mixtures, which results in problems upon application.

A further disadvantage of synthetic surfactants is that these substances, in order for the registration thereof as adjuvants to be approved by the national authorities, are required to demonstrate that they do not produce residues in the soil. This residue problem issue, which in most countries only exists for pesticidal active substances, is increasingly applied to adjuvants. Moreover, toxicologically acceptable additives and adjuvants are increasingly demanded in the agricultural sector.

Besides adjuvants, other additives are frequently employed in crop protection formulations. One class of additives which has gained particular importance in recent years are so-called "spray drift additives", which are employed for regulating the droplet size during the spraying of the crop protection formulation. Customary atomization methods generally generate droplets with a very broad droplet size distribution. In this context, it is known that the droplets' driftability, i.e. uncontrolled transport by gentle air currents, correlates with the droplets' size and is more pronounced for small droplets. In a series of field trials, wind-tunnel experiments and mathematical models it has been possible to demonstrate in this context that it is in particular droplet sizes of smaller than 150 μm which are increasingly susceptible to drift and are therefore increasingly prone to so-called "off-target" deposition (M. E. Teske, A. J. Hewitt, D. L. Valcore, "*The Role of Small Droplets in Classifying Drop Size Distributions*", ILASS Americas 17*th* Annual Conference, 2004, Arlington Va.). Drift results in a high environmental impact for the surroundings and in economic losses. To overcome this problem, a series of additives for drift control have been developed in the past. In most cases, high-molecular-weight, water-soluble polymers are admixed to the crop protection formulation as a tank mix additive, and these polymers increase the spray's viscosity and thus result in the formation of larger droplets during spraying (see, for example, US 2001/0051145, US 2002/0108415 and WO 2008/101818 (US 2010/0152048)). A disadvantage of this approach, however, is that, as a rule, an only insufficient distribution of the spray on the plants can be achieved frequently owing to the increased viscosity of the crop protection formulation. Moreover, corresponding polymers frequently only dissolve slowly during the tank mixing process. Insufficiently dissolved polymer residues cause, inter alia, the spray nozzles to become clogged, which results in problems during the spraying process.

US 2012/0065068 describes the use of selected tertiary amines and amine oxides as antidrift agents, whereas U.S. Pat. No. 6,797,673 B1 reports the use of lecithins for drift control. US 2010/0113275 describes a series of self-emulsifying esters as antidrift additives, with oleo chemistry-based alkoxylates being mentioned in detail.

The use of polyglycerol esters as antidrift additives is not known from the prior art.

It was an object of the present invention to provide novel adjuvants for crop protection formulations, which adjuvants overcome at least one disadvantage of the prior art.

Surprisingly, it has been found that self-emulsifying compositions as described in the claims achieve this object.

A subject of the present invention is therefore compositions comprising at least one hydrophobic, at least partially water-insoluble polyglycerol ester in combination with at least one emulsifier.

A further subject of the present invention is the use of the compositions according to the invention, comprising hydrophobic, at least partially water-insoluble polyglycerol esters in combination with at least one emulsifier, as additives for crop protection formulations.

Preferred is the use of the compositions according to the invention, comprising hydrophobic, at least partially water-insoluble polyglycerol esters in combination with at least one emulsifier, as additives for crop protection formulations for avoiding spray drift.

The subjects according to the invention will be described hereinbelow without the invention being limited to these exemplary embodiments. If ranges, general formulae or classes of compounds are mentioned hereinbelow, they are intended to comprise not only the corresponding ranges or groups of compounds which are mentioned explicitly, but also all part-ranges and part-groups of compounds which can be obtained by selecting individual values (ranges) or compounds. When documents are cited for the purposes of the present description, the entire content of these is intended to be part of the disclosure of the present invention. When % data are provided hereinbelow, they are, unless otherwise specified, data in % by weight. In the case of compositions, the % data, unless otherwise specified, refer to the total composition. When averages are mentioned, they are, unless otherwise specified, mass averages (weight averages). When measured values are stated hereinafter, then these measured values, unless otherwise specified, were determined at a pressure of 101325 Pa and a temperature of 25° C.

The statement of a mass ratio of, for example, component (a) to component (b) of 0.1 means that a mixture comprising these two components includes 10% by weight of component (a) based on the total of the masses of components (a) and (b).

Partially water-insoluble means that the polyglycerol esters at a given temperature at a concentration of at least 0.01 g/l to 20 g/l in water already results in an opacity which can be discerned by the human eye, and preferably forms two phases at a concentration of at least 0.5 g/l to 2 g/l.

The solubility is preferably determined at a temperature of below 80° C., preferably below 70, 60, 50, 40, 30, 29, 28, 27, 26, 25, 24, 23, 22, 21 and below 20° C. Furthermore, the solubility is preferably determined above 0° C., more preferably above 5, 10, 15, 16, 17, 18, 19, 20, 21, 22, 23, 24 and above 25° C. More preferably, the solubility is determined at ambient temperature. Especially preferably, the solubility is determined at between 15° C. and 30° C., more preferably at from 20° C. to 25° C.

Preferably, the hydrophobic, at least partially water-insoluble polyglycerol esters have an HLB value of 8 or less, preferably 7 or less, and especially preferably 6.5 or less. Furthermore, preferably, the HLB value is at least 0.5, preferably at least 1 and especially preferably at least 2.

The HLB value may be determined by various prior-art methods, it is an accepted measure of the hydrophobicity (wikipedia/en: "HLB", Sep. 16, 2014). The HLB value of the hydrophobic polyglycerol esters is preferably calculated following the formula $$HLB = 20 \cdot \left(1 - \frac{m_1}{m}\right)$$

where $m_1$ and m are the molar mass of the lipophilic portion ($m_1$) and the total molecular mass (m) of the polyglycerol ester, respectively.

The molar masses are determined by prior-art methods, they are preferably determined by mass spectrometry, and the determination of the lipophilic portion is done on the basis of the mass-spectroscopy results applying the stoichiometric rules with which the skilled worker is familiar.

Preferably, the compositions according to the invention comprise polyglycerol esters of the general formula 2

$$M_a D_b T_c \qquad \text{Formula 2}$$

where $M=[C_3H_5\,(OR)_2O_{1/2}]$ $D=[C_3H_5\,(OR)_1O_{2/2}]$ $T=[C_3H_5O_{3/2}]$ a=1 to 10, preferably 2 to 3, especially preferably 2 b=0 to 10, preferably greater than 0 to 5, especially preferably 1 to 3, c=0 to 3, preferably 0, where, preferably, the sum total of a+b+c is 1 to 20, preferably 2 to 5,
where the radicals R independently of one another are identical or different radicals of the formula R'—C(O)— or H,
  where R' is a monovalent aliphatic, saturated or unsaturated hydrocarbon radical having 3 to 39 C atoms, preferably 7 to 21, especially preferably having 9 to 17 carbon atoms,
where at least one radical R corresponds to a radical of the formula R'—C(O)—.

More preferably, the compositions according to the invention comprise polyglycerol esters of the general formula 3

$$M_xD_yT_z \qquad \text{Formula 3}$$

where x=1 to 10, preferably 2 to 3, especially preferably 2,
y=0 to 10, preferably greater than 0 to 5, especially preferably 1 to 3,
z=0 to 3, preferably 0,
where preferably the total of x+y+z is 1 to 20, preferably 2 to 5,
with the proviso that at least one radical R is a radical other than hydrogen, and furthermore R is defined as it is for formula 2.

Even more preferably, the polyglycerol esters of the compositions according to the invention of the general formula 1 comprise Formula 1 where
k=1 to 10, preferably 2 to 3, especially preferably 2,
m=0 to 10, preferably greater than 0 to 5, especially preferably 1 to 3,
with the proviso that at least one of the radicals R is a radical of the formula R'—C(O)— and that the total of k+m is 1 to 20, preferably 2 to 5 and the fragments with the indices k and m are randomly distributed.

Random distributions are composed blockwise, having any desired number of blocks and any desired sequence, or being subject to a randomized distribution; they may also be composed alternatingly, or else form a gradient over the chain; in particular, they may also form all mixed forms, where groups of different distributions may optionally follow each other. The random distributions may be subject to restrictions resulting from specific embodiments. Wherever the restriction does not apply, there is no change to the random distribution.

The indices in the formulae 1, 2 and 3 are mean values as usual for polymers, preferably, they are arithmetic mean values.

Preferably, the polyglycerol esters of the compositions according to the invention include more than one radical R of the formula R'—C(O)—, more preferably at least 2, even more preferably at least 3.

The radicals R of the formula R'—C(O)— are preferably independently of one another identical or different acyl radicals of saturated or unsaturated fatty acids, where the fatty acids include 4 up to 40 carbon atoms, more preferably, the fatty acids are selected from among butyric acid (butanoic acid), caproic acid (hexanoic acid), caprylic acid (octanoic acid), capric acid (decanoic acid), lauric acid (dodecanoic acid), myristic acid (tetradecanoic acid), palmitic acid (hexadecanoic acid), stearic acid (octadecanoic acid), arachidic acid (eicosanoic acid), behenic acid (docosanoic acid), lignoceric acid (tetracosanoic acid), palmitoleic acid ((Z)-9-hexadecenoic acid), oleic acid ((Z)-9-hexadecenoic acid), elaidic acid ((E)-9-octadecenoic acid), cis-vaccenic acid ((Z)-11-octadecenoic acid), linoleic acid ((9Z,12Z)-9,12-octadecadienoic acid), alpha-linolenic acid ((9Z,12Z,15Z)-9,12,15-octadecatrienoic acid), gamma-linolenic acid ((6Z,9Z,12Z)-6,9,12-octadecatrienoic acid), di-homo-gamma-linolenic acid ((8Z,11Z,14Z)-8,11,14-eicosatrienoic acid), arachidonic acid ((5Z,8Z,11Z,14Z)-5,8,11,14-eicosatetraenoic acid), erucic acid ((Z)-13-docosenoic acid), nervonic acid ((Z)-15-tetracosenoic acid), ricinoleic acid, hydroxystearic acid and undecenoic acid, and mixtures, such as, for example, rapeseed oil acids, soya fatty acids, sunflower fatty acids, peanut fatty acids and tall oil fatty acids. Especially preferred in this context are radicals of oleic acid.

When calculating the HLB value, the molar mass of the lipophilic molecule moiety is the arithmetic mean of the total of the molar masses of all of the radicals R' which are present in the molecule. The total molar mass is calculated as defined hereinabove.

Sources of suitable fatty acids or fatty acid esters, especially glycerides, may be vegetable or animal fat, oils or waxes. Examples of those which may be used are: lard, beef dripping, goose fat, duck fat, chicken fat, horse fat, whale oil, fish oil, palm oil, olive oil, avocado oil, seed kernel oils, coconut oil, palm kernel oil, cocoa butter, cottonseed oil, pumpkinseed oil, corn oil, sunflower oil, wheatgerm oil, grapeseed oil, sesame oil, linseed oil, soya oil, peanut oil, lupin oil, rapeseed oil, mustard oil, castor oil, jatropha oil, walnut oil, jojoba oil, lecithin, for example based on soya, rapeseed or sunflowers, bone oil, neat's-foot oil, borage oil, lanolin, emu oil, deer tallow, marmot oil, mink oil, safflower oil, hemp oil, pumpkin oil, evening primrose oil, tall oil, and also carnauba wax, beeswax, candelilla wax, ouricury wax, sugarcane wax, retamo wax, caranday wax, raffia wax, esparto wax, alfalfa wax, bamboo wax, hemp wax, Douglas fir wax, cork wax, sisal wax, flax wax, cotton wax, dammar wax, tea wax, coffee wax, rice wax, oleander wax, beeswax or wool wax.

Especially preferred are the polyglycerol esters of the compositions according to the invention with an HLB of from 4 to 6.5 of formulae 1, 2 or 3, where the polyglycerol esters have an arithmetic mean of 2.9 to 3.1 radicals of the formula R'—C(O)—.

Furthermore especially preferred are the polyglycerol esters of the compositions according to the invention with an HLB of from 4 to 6.5 of the formula 1, where the total of k+m is 3 and which have an arithmetic mean of 2.9 to 3.1 radicals of the formula R'—C(O)—.

More especially preferred are the polyglycerol esters of the compositions according to the invention with an HLB of from 4 to 6.5 of the formulae 1, 2 or 3 which have an arithmetic mean of 2.9 to 3.1 radicals R of the formula R'—C(O)—, where the acyl radicals are of fatty acid mixtures comprising oleic acid, stearic acid, palmitic acid and gamma-linolenic acid, where these abovementioned fatty acids preferably amount to at least 85% by weight in the fatty acid mixture.

Especially preferred are the polyglycerol esters of the compositions according to the invention with an HLB of from 4 to 6.5 of the formula 1, where the total of k+m is 3 and which have an arithmetic mean of 2.9 to 3.1 radicals of the formula R'—C(O)— where the acyl radicals of fatty acid mixtures comprise oleic acid at least 70% by weight, preferably at least 75% by weight, more preferably at least 80% by weight, even more preferably at least 85% by weight, particularly preferably at least 90% by weight and especially preferably at least 95% by weight, the sum total of all fatty acids being 100% by weight.

A further advantage of the compositions according to the invention is their biodegradability.

The biodegradability is preferably determined by the OECD 301 F method. More preferably, the biodegradability is determined as specified in 28 d of OECD 301 F.

The polyglycerol esters of the compositions according to the invention preferably have a biodegradability of at least 50%, even more preferably of at least 55% and especially preferably of at least 60%, the maximum biodegradability value being 100%.

The emulsifiers which are present in the compositions according to the invention are preferably fatty acid esters of polyhydric alcohols and their polyalkylene glycol derivatives, polyglycol derivatives of fatty acids and fatty alcohols, sorbitan fatty acid esters, alkylphenol ethoxylates and block copolymers of ethylene oxide and propylene oxide, ethoxylated amines, amine oxides, acetylene diol surfactants and silicone surfactants. The emulsifier is particularly preferably a sorbitan fatty acid ester, and the emulsifier is especially preferably an ethoxylated sorbitan fatty acid ester.

The fatty acids of the sorbitan fatty acid esters are preferably defined like the fatty acids of the polyglycerol esters, and are preferably the acyl radicals of fatty acid mixtures comprising oleic acid, stearic acid, palmitic acid and gamma-linolenic acid, where these abovementioned fatty acids preferably amount to at least 85% by weight in the fatty acid mixture. Especially preferred are ethoxylated sorbitan fatty acid esters, where the acyl radicals of fatty acid mixtures comprising oleic acid in an amount of at least 70% by weight, preferably at least 75% by weight, more preferably at least 80% by weight, even more preferably at least 85% by weight, particularly preferably at least 90% by weight and especially preferably at least 95% by weight.

The emulsifier is still more preferably an ethoxylated sorbitan trioleate, especially a polyethylene glycol-20 sorbitan trioleate.

The emulsifiers are furthermore preferably distinguished by the fact that they have an HLB of 9 or greater, preferably 10 or greater, and especially preferably 11 or greater. The HLB is determined by the same method as described hereinabove for the polyglycerol esters.

The concentration of the emulsifier in the compositions according to the invention is preferably below 40% by weight, particularly preferably below 30% by weight, especially preferably below 25% by weight, and amounts to at least 5% by weight, preferably at least 10% by weight, more preferably at least 15% by weight. In this context, preferred concentration ranges are from 5 to 40% by weight, more preferred ones from 10 to 30% by weight and especially preferred ones from 15 to 25% by weight.

Preferred are the compositions according to the invention comprising at least one hydrophobic, at least partially water-insoluble polyglycerol ester with an HLB of less than 8 and comprising at least one emulsifier with an HLB of 9 or greater.

More preferred are the compositions according to the invention comprising at least one polyglycerol ester with an HLB of from 4 to 6.5 of the formulae 1, 2 or 3, and which have an arithmetic mean of 2.9 to 3.1 radicals R of the formula R'—C(O)—, where the acyl radicals are of fatty acid mixtures comprising oleic acid, stearic acid, palmitic acid and gamma-linolenic acid, where these abovementioned fatty acids preferably amount to at least 85% by weight in the fatty acid mixture and at least one emulsifier with an HLB of 9 or greater, where the emulsifier is an ethoxylated sorbitan fatty acid ester.

A further advantage of the compositions according to the invention is the enhancement of the efficacy of pesticides.

Pesticides are preferably herbicides, fungicides, insecticides, growth regulators, molluscicides, bactericides, virucides, micronutrients and biological crop protection products based on natural materials or living or processed microorganisms, and the mixtures thereof.

An advantage of the composition according to the invention is that these compositions increase the activity of pesticides and simultaneously have anti-spray-drift properties.

Within the scope of the present invention, "self-emulsifying" means that the compositions according to the invention can be dispersed in water without introducing major shear, and spontaneously form emulsion droplets of a volume-weighted mean size of <400 μm, preferably <200 μm, especially preferably <100 μm, with the droplets having a mean size of at least 0.1 μm.

The size of the emulsion droplets is preferably measured by laser diffraction, especially preferably by using the MasterSizer 3000 from Malvern.

The polyglycerol esters of the compositions according to the invention are preferably prepared from natural raw materials. This is advantageous in the sense of a so-called sustainable economy.

A further advantage of the polyglycerol esters is that they do not present any health hazard. Indeed, in many cases they are approved as a food additive, for example under the number E475 (polyglycerol esters of edible fatty acids). All this is advantageous in the light of the residue problems described in the prior art.

Since adjuvants of the prior art, as a rule, are water-soluble so as to improve the activity of crop protection agents from aqueous spray mixtures, it is surprising in the light of the prior art that similar effects can also be achieved using self-emulsifying composition comprising an at least partially water-insoluble, hydrophobic polyglycerol ester and at least one emulsifier.

The compositions according to the invention are preferably used as tank mix additive for spray mixtures. Preferred use concentrations in this context are between 0.001 and 1% (v/v), preferably between 0.01 and 0.5% (v/v) and especially preferably between 0.02 and 0.15% (v/v) (approximately also corresponding to 0.1% by weight) of the spray mixture. This equals 10 to 3000 ml/ha if 100 to 1000 l of spray mixture are usually applied per ha and preferably an amount of adjuvant of from 50 to 700 ml/ha, which are also added to the respective spray mixture amounts independently of the total water application rate per ha.

A further advantage of using the compositions according to the invention is that the adhesion, on plant surfaces, including plant surfaces which are difficult to wet, of sprays comprising active substances is improved. The result is that the amount of crop protection agent used for crop husbandry may be reduced, which has both ecological and economical advantages.

A further advantage of the compositions according to the invention is that the polyglycerol esters are present not in dissolved form, but emulsified in the form of fine droplets, whereby the development of foam when making spray mixtures can be reduced in comparison to water-soluble adjuvants which are usually employed.

A further advantage of the compositions according to the invention is that, due to their self-emulsifying properties, they can be incorporated into crop protection formulations and spray mixtures with gentle stirring in a problem-free manner. In the case of tank mix formulations, for example, a sufficiently homogeneous distribution of the polyglycerol ester in the spray mixture is obtained as early as during the tank mixing process. This firstly facilitates the making up of spray mixtures. Furthermore, the good incorporability, and the homogeneous distribution which this entails, avoids the spray nozzles becoming clogged during the spraying process.

Active substances are those which are approved and/or registered and/or listed in the individual countries for application to plants and crops in order to protect plants against damage, or in order to avoid the yield loss caused by pests or the like in a crop, or to eliminate undesired accompanying vegetation, such as broad-leaved weeds and/or grass weeds, or to provide the plant with nutrients (also called fertilizers). Active substances may be of synthetic or else biological nature. Active substances may also be extracts, or natural substances, or organisms which act as antagonists. They are also usually referred to as pesticides or crop protection agents. Generally, active substances are incorporated into formulations for handling and efficacy purposes.

Preferred active substances are selected from the chemical active ingredient classes of strobilurins, carboxamides, triazoles, benzophenones, morpholines, neonicotinoids, sulphonylureas, growth substances and total herbicides, and combinations thereof.

The active substances are further preferably selected from azoxystrobin, pyraclostrobin isopyrazam, epoxyconazole, difenoconazole, metrafenone, fenpropimorph, thiamethoxam, rimsulfuron, dicamba and glyphosate, and combinations thereof.

For the application to plants or plant parts, crop protection agent formulations are usually diluted with water before the customary spraying via nozzles, and they also comprise, besides the active component, other auxiliaries such as emulsifiers, dispersants, antifrost agents, defoamers, biocides and surface-active substances such as surfactants. Active substances, in particular fungicides, insecticides and nutrients, may also be applied to seed(s) of plants by various methods, either alone or in combination and provided with the above-stated other auxiliaries. Such methods are also referred to as seed treatment methods. The seed treatment with fungicides and insecticides can protect plants at the early growth stage from diseases and attack by insects.

The field trials carried out within the scope of the invention demonstrate that the compositions according to the invention have a yield-increasing effect on agriculturally useful plants. This increase in yield is achieved both in combination with active substances and without active substances. Furthermore, it has been demonstrated that the compositions according to the invention markedly increase the activity of pesticides.

The examples demonstrate that the use of the compositions according to the invention for increasing the yield of agriculturally useful plants and also the enhancement of the pesticides' activity is successful for a multiplicity of crop plants. The activity can be observed both on monocotyledonous and on dicotyledonous plants.

Since the activity-enhancing effects have become apparent in a variety of crop plants of two different groups (the use of the term "group" is to be understood in the botanical sense) of the angiosperms, both monocotyledonous and dicotyledonous, it can be assumed that the effects will also be possible with other plants.

Furthermore, it has been demonstrated that the compositions according to the invention bring about an enhancement of the activity with a multiplicity of different pesticides from very different classes of chemical structures. It can be assumed that other pesticidal active substances, too, will demonstrate activity-enhancing effects with the compositions according to the invention when the compositions according to the invention are employed in combination with approximately 50-500 g/ha pesticide, but in particular with 100-200 g/ha pesticide.

Even more preferred is the use of the compositions according to the invention for enhancing the efficacy of pesticides and simultaneously for avoiding spray drift.

Especially preferred is the use of the compositions according to the invention for increasing the activity of pesticides and simultaneously for avoiding spray drift and for increasing the yield of agricultural crops.

Reducing the driftability of the spray droplets is advantageous, since this causes reduced contamination of the environment. Moreover, the loss of expensive active substances can be avoided, since a higher percentage of them can be applied to the target area by using the compositions according to the invention.

Within the scope of the invention, drift is understood as meaning the transversal movement of a spray away from its place of origin. Drift is preferably caused by environmental and/or ambient influences. These environmental and/or ambient influences are preferably wind. This wind may be of natural or man-made origin. Wind of man-made origin is preferably airflows which are generated by the movement of a vehicle on the ground or in the air. Preferably, these are vehicles or aircraft used in the cultivation of an agricultural area.

The medium of the spray here is an aqueous medium in all cases. Preferably, the spray originates by atomization in the air.

Particularly preferably, drift is understood as meaning the transversal movement of a spray from the place of its origin caused by wind, the spray having been generated by atomization of an aqueous medium in the air.

The activity of an anti-drift additive may preferably be quantified by the effect of the additive on the droplet size distribution of the spray. There is a direct relationship between the size of a droplet and its tendency to drift—the finer the droplet, the greater the risk of drift.

Within the scope of the present invention, the term "droplet size distribution" refers to volume-weighted size distributions when the droplet diameter in the spray mist is measured. Preferably, volume-weighted droplet size distributions can be determined by laser diffraction measurements (for example by using laser diffraction systems from Sympatec or Malvern as specified in ASTM method E2798, reference being made therein to E1260), or by the computer-aided image evaluation of highly-resolved, static images of the spray mist.

More preferably, the droplet size is determined by image analysis of highly resolved spray images. Such spray images are preferably created with the aid of a highly resolving high-speed camera, for which purpose a camera of the type Vision Research Phantom V12 is particularly preferred. To this end, the camera is positioned perpendicular to the spray lamella 12 cm below the nozzle exit (flat-spray nozzle of the type XR 11003 from TeeJet), and the spray is recorded at a magnification of 1.15 for a minimum of 20 seconds. The droplet size is then determined by means of image analysis of at least 2000 independent static individual images of the spray as described in the examples. Such determinations of the droplet size are likewise used to determine the droplet volumes.

The graphical plot of the volume percentage vs. the droplet diameter gives a typical particle distribution curve. Such distributions are shown in the figures of this invention. It is therefore possible to determine typical parameters of the distribution such as, for example, the volume fraction of the droplets which are smaller than a certain threshold value, and the maximum of the distribution and the mean volumetric diameter (MVD). The mean volumetric diameter here is a measurement used to classify sprays and is defined in that, of the atomized total volume of a liquid, 50% of the drops are larger than this value and 50% are smaller than this value. Consequently, the MVD represents a volume-related median value.

The droplet size distribution of a spray is dependent on the composition of the spray and also on the conditions during the spray operation. Thus, for example, the type of construction of the spray nozzle used and also the selected spray pressure have a significant influence on the resulting droplet size distribution.

Preferably, the spray is generated using nozzles, preferably nozzles of the construction types flat-spray nozzles, wide-angle flat-spray nozzles, double flat-spray nozzles, hollow cone nozzles, filled cone nozzles, high-pressure nozzles, edge nozzles, as well as air injector nozzles; more preferred are nozzles of the construction type of a flat-spray nozzle. Nozzles of this type are available for example from the manufacturers Lechler, TeeJet and/or Agrotop. Special preference is given to flat-spray nozzles from TeeJet, with nozzles of the type XR 11003 being very particularly preferred.

Furthermore preferably, a pressure of from 0.5 to bar, preferably of from 0.8 to 8 bar, more preferably of from 0.9 to 6 bar, even more preferably of from 0.95 to 2.5 bar and especially preferably of from 1 to 1.5 bar is used for generating spray.

The influence of the anti-drift additives on the droplet size distribution of a spray is always relatively based on a spray of a formulation which is distinguished by the absence of these additives in an otherwise identical composition, and is sprayed under identical conditions.

The addition of the compositions according to the invention to crop protection formulations or spray mixtures for drift control preferably brings about a decrease in the volume fraction of droplets with a droplet diameter of less than 150 μm of at least 10%, preferably 15%, particularly preferably 20%, based on the droplet diameter of an identical spray without addition of the anti-drift additive.

Furthermore, the addition of the compositions according to the invention to crop protection formulations or spray mixtures for drift control brings about a relative shift in the maximum of the droplet size distribution of at least 5%, preferably 10%, particularly preferably 15%, based on the droplet size distribution of an identical spray without addition of the anti-drift additive.

Furthermore, the addition of the compositions according to the invention to crop protection formulations or spray mixtures for drift control brings about a relative increase of the volume-related median of the droplet size distribution of at least 5%, preferably 10%, particularly preferably 15%, based on the droplet size distribution of an identical spray without addition of the anti-drift additive.

Furthermore in more preferred is the use of the compositions according to the invention to crop protection formulations or spray mixtures for drift control, where the volume-related median of the droplet size distribution is at least 5% greater than that of a spray based on fully-demineralized water, where the spray is produced using a flat-spray nozzle of the type XR 11003 from TeeJet at a pressure of 1 bar and a temperature of 25° C., the volume-related median being determined by image analysis of highly resolving images of the spray.

EXAMPLES

General Methods and Materials:
Substances:

In the experiments which follow, a mixture of 80% by weight of triglyceryl trioleate with 20% by weight of polyethylene glycol—20 sorbitan trioleate was used and diluted with water.

Spraying Experiments:

All spraying experiments were carried out using a flat-spray nozzle of the type XR 11003 from TeeJet. All the spraying experiments were carried out here at a spraying pressure of 1 bar. The droplet size of the resulting spray was determined by image analysis of highly resolved images of the spray. To this end, a high-speed camera of the type Vision Research Phantom V12 was positioned perpendicularly to the spray lamella 12 cm below the nozzle exit, and the spray was filmed for 20 sec at a magnification of 1.15 for at least 20 seconds. The droplet size distribution was subsequently determined by image analysis of at least 2000 independent static individual images of the spray. To this end, the individual drops were detected on the basis of their intensity deviating from the background. The projected area of each drop was then determined from the recorded images, which was used to calculate an equivalent diameter: $D=(4*A/pi)^{0.5}$, where D is the equivalent diameter and A is the projected area. The result obtained was a volume-weighted droplet size distribution, by means of which the maximum of the distribution and the mean volumetric diameter (MVD) can be determined. This image analysis was carried out here using the computer program Matlab (for details and background, see, for example, R. C. Gonzalez, S. L. Eddins and R. E. Wood, "Digital Image Processing using Matlab", 2004, Prentice Hall Verlag, or see K. J. Hay, Z.-C.-Liu, T. J. Hanratty, "A Backlighted Imaging Technique for Particle Size Measurements in Two Phase Flows", *Experiments in Fluids*, 1998, 25(3), 226-232).

Determination of the Particle Size in Emulsions:

The particle size in emulsions was determined by laser diffraction measurements using the Malvern MasterSizer 3000. The measurements were carried out here in dilute aqueous solutions. The evaluation of the scattered signal was carried out automatically by the software supplied with the instrument. The result obtained was a volume-weighted particle size distribution. In order to ensure that the droplet size of the emulsion does not change as a result of diluting, an estimation of the droplet size was additionally carried out by viewing micrographs of the undiluted emulsion.

Comparative Example 1: Spraying Experiment with Pure Water

Figure 1:
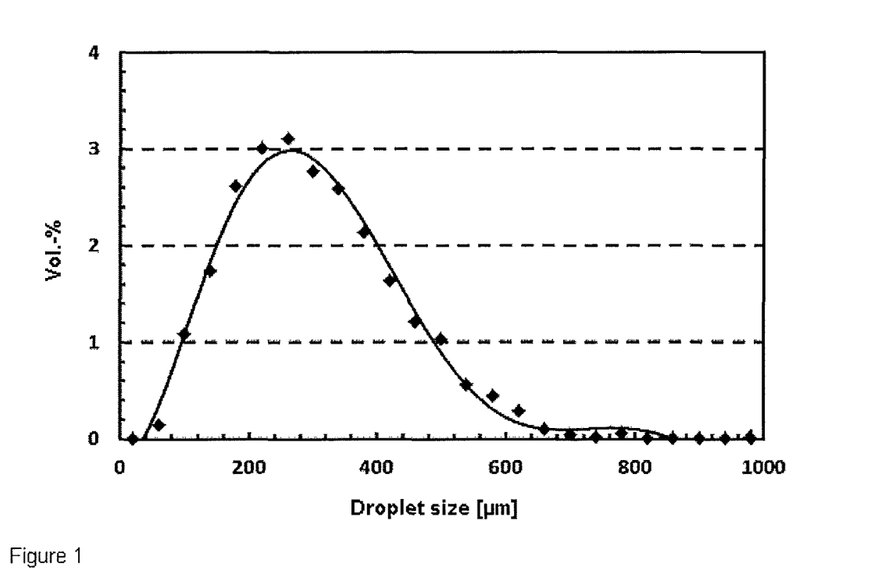
FIG. 1: volume-weighted droplet size distribution of a spray based on fully-demineralized water

Fully-demineralized water was atomized under the above-described conditions. FIG. 1 shows the volume-weighted droplet size distribution determined with the help of image analysis.

The maximum of the droplet size distribution is at 260 µm. Moreover, a mean volumetric diameter of 252 µm will be determined.

Figure 2:
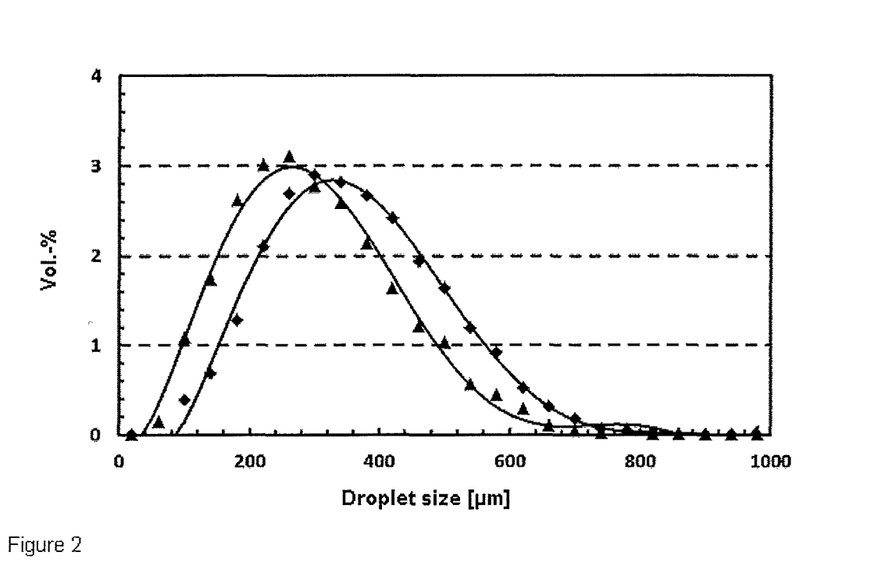
FIG. 2: volume-weighted droplet size distribution of a spray based on fully-demineralized water (triangles) and of a spray composed of water+0.1% of a hydrophobic, water-insoluble and self-emulsifying polyglycerol ester.

Example 2 According to the Invention: Spraying Experiment with Water+Polyglycerol Ester With gentle stirring, 0.1 parts by weight of the composition according to the invention was incorporated into 99.8 parts by weight of water. The emulsion of the defoamer active-substance mixture obtained had a droplet size of less than 100 µm (determined by laser diffraction using a Malvern MasterSizer 3000). This mixture was atomized under the experimental conditions stated hereinabove. FIG. 2 shows the volume-weighted droplet size distribution determined with the aid of high-speed video recordings.

The maximum of the droplet size distribution in comparison with fully-demineralized water shifted from 260 µm to 340 µm. The MVD shifted from 252 µm for pure water to 351 µm as a result of the anti-drift additive (FIG. 2).

Example 3: Biological Activity

Field trials were designed in which crop plants, for example cereal species (barley and wheat), legume (soya) and the fibre plant cotton, were treated with crop protection agents (CPA) in order to protect them against diseases or to control insects. Likewise, field trials were designed in which broad-leaved weeds and grass weeds were treated with a nonselective herbicide (damages all green plants) or with selective herbicides (controls only the weed, but is not harmful for the crop plant). The application of these substances which are generally referred to as "crop protectants" was carried out either after dilution with water alone or mixed in the same spray tank with different doses of the adjuvants according to the invention. The application was carried out at points in time at which such products are conventionally applied by spraying in order to protect crop plants or to control weeds.

TABLE X

Crop protection agents used in Examples 3.1 to 3.7:

| Code | Trade name | Pesticides (component of active substances) | Manufacturer |
|---|---|---|---|
| CPA-1 | Amistar Opti | 250 g/l azoxystrobin + 500 g/l chlorothalonil | Syngenta, Basel Switzerland |
| CPA-2 | Capalo | 75 g/l metrafenone + 62.5 g/l epoxyconazole + 200 g/l fenpropimorph | BASF, Ludwigshafen, Germany |
| CPA-3 | Seguris | 125 g/l isopyrazam + 90 g/l epoxyconazole | Syngenta, Basel Switzerland |
| CPA-4 | Score | 250 g/l difenoconazole | Syngenta, Basel Switzerland |
| CPA-5 | Actara | 250 g/kg thiamethoxam | Syngenta, Basel Switzerland |
| CPA-6 | Cato Komp. A + Banvel 4S | 250 g/kg rimsulfuron + 480 g/l dicamba | DuPont, Germany Stähler Suisse SA, Zofingen, Switzerland |
| CPA-7 | Roundup | 450 g/l glyphosate salt | Monsanto, USA |

The active substances belong to the following classes of chemical active substances, which are thereby represented:

strobilurins: azoxystrobin, pyraclostrobin
carboxamides: isopyrazam
triazoles: epoxyconazole, difenoconazole
benzophenones: metrafenone
morpholins: fenpropimorph
neonicotinoids: thiamethoxam
sulphonylureas: rimsulphoron
growth regulators: dicamba
nonselective herbicide: glyphosate

TABLE XX

Identity of the adjuvants as used:

| Code | Adjuvant | Composition |
|---|---|---|
| ADJ-1 | Adjuvant according to the invention | 80% polyglycerol ester + 20% emulsifier |
| ADJ-2 | Commercial adjuvant, not according to the invention | Organo-modified trisiloxane, BREAK-THRU S240 (Evonik Industries AG, Essen, Germany) |

General Description of the Field Trials:

The design of field trials for testing fungicides in cereal species or legume species is known in principle to the skilled worker. The same applies to the design of trials for testing insecticides in cotton and for testing nonselective herbicides (a nonselective herbicide is one that kills all plants, including crop plant, when the plants come into contact with it) and selective herbicides (do not kill the crop plant when they come into contact with the agent, but kill the undesired broad-leaved plant or grass which is to be eliminated) in maize and other crop plants. Therefore, the procedure will only be described in summary here:

In fields with uniformly grown cereals (barley, wheat), legumes (soybeans), cotton and maize, plots of 10 to 37 $m^2$ in size were distributed randomly in four replicated blocks with four replications. The grass species *Brachiaria plantaginea* and *Digitaria horizontalis* and the broad-leaf weed Acanthospermum hispidum were sown in plots for the trials with the nonselective herbicide CPA-8.

The plants in the four plots of each treatment remained untreated or were treated with crop protection agents (see Table X) alone or in combination with adjuvants (see Table XX). The test products were diluted with water (use composition) and applied to the plants by means of a flat-spray nozzle, preferably an AI nozzle, in a water volume of 150 to 300 l/ha. In some case, the spray treatment was repeated at an interval of 2 to 4 weeks.

The result of the treatment was determined on different days after spraying the plants, using a representative number of plants per plot. The disease level in the untreated control was likewise scored. The results of the treatment are given in the examples as the mean of the 4 plots which were sprayed separately in each experiment.

The disease symptoms caused by fungal attack is given as the total of the areas diseased with one and/or more diseases (in % of the leaf area). A lower percentage in a comparison is therefore a positive result.

In the experiments with insect attack, 10 leaves were sampled from each plot on different days after the spray treatment. The number of insects was counted. The lower the number, the higher the activity of the agents. In the herbicide experiments, the activity of the spray treatment was scored in such a way that the biomass production of the treated plots (m*) was related to the biomass production in the untreated plots (m°), and the activity was calculated using the formula $$\text{efficacy} = 1 - (m^*/m^\circ)$$

Here, an activity of 100% is attained when all of the biomass in the treated plot has been killed, and 0% activity when no effect whatsoever on the biomass by the treatment has been found. A higher percentage in a comparison is therefore a positive result.

At the point in time of the cereals' and the legume's kernel maturity, the plots of each treatment were harvested, and the kernel weights were weighed for each plot. The moisture of the kernels was determined, and the yields were calculated for each plot for a specific uniform fresh weight (in the case of cereals, 14% moisture; in the case of legumes (soybean) 9% moisture) so as to compensate for irregularities in the fresh weight between the individual plots. Thereafter, the kernel weight was extrapolated to a uniform area of one hectare in size. A higher yield in a comparison is therefore a positive result.

The infection with the plant pathogens (fungi and insects) was not induced, but originated from the environment.

Example 3.1: Winter Barley

In a field with winter barley cv. "Tenor" at growth stage 41 (all leaves fully developed), the CPA-1 and the adjuvants ADJ-1 and ADJ-2 were diluted in 200 l/ha water and the mixture was sprayed onto the plants. Before the application, the plants were infected with powdery mildew (caused by the pathogenic fungus Blumeria graminis) and by ramularia (caused by the pathogenic fungus Ramularia collo-cygni). The disease symptoms of the leaves were determined on the second leaf below the flag leaf, 14 days after the application. The grain yields were determined after the crop had been harvested. The application rates of the products and the results are shown in Table A.

TABLE A

Disease symptoms of the leaves, and grain yield as per Example 3.1:

| Treatment | Disease symptoms, powdery mildew [%] | Disease symptoms, ramularia (%) | Grain yield [dt/ha] |
|---|---|---|---|
| Untreated | 15 | 17.5 | 47.4 |
| 1.5 l/ha CPA-1 | 8.5 | 16.3 | 58.6 |
| 1.5 l/ha CPA-1 + 0.25 l/ha ADJ-1 | 6.0 | 9.0 | 64.0 |
| 1.5 l/ha CPA-1 + 0.5 l/ha ADJ-1 | 1.5 | 5.0 | 65.2 |
| 1.5 l/ha CPA-1 + 0.2 l/ha ADJ-2 | 2.0 | 11.8 | 63.9 |

The results demonstrate that the fungicide alone reduced the disease symptoms. The combination of the fungicide with the composition according to the invention, and the comparative adjuvant, showed a marked increase. A higher dosage of the ADJ-1 had a higher activity, as expected, with the higher dosage exceeding the activity of the comparison. The grain yields increased in the same manner.

Example 3.2: Winter Wheat

In a field with winter wheat cv. "Akteur" at growth stage 32 (2-node stage) and again at growth stage 51 (all leaves fully developed, beginning of ear emergence), the CPA-2 and the adjuvants ADJ-1 and ADJ-2 were diluted with 200 l/ha water and the mixture was sprayed onto the plants. Before the application, the plants were infected by septoria leaf spot (caused by the pathogenic fungus Mycosphaerella graminicola). The disease symptoms were determined 27 days after the first application and 26 days after the second application, on the first leaf below the flag leaf. The grain yields were determined after the crop had been harvested. The application rates of the products and the results are shown in Table B.

TABLE B

Disease symptoms of the leaves, and grain yield as per Example 3.2:

| Treatment | Disease symptoms, first determination [%] | Disease symptoms, second determination (%) | Grain yield [dt/ha] |
|---|---|---|---|
| Untreated | 14.0 | 91.3 | 81.8 |
| 1 l/ha CPA-2 | 7.5 | 22.8 | 93.1 |
| 1 l/ha CPA-2 + 0.25 l/ha ADJ-1 | 4.5 | 17.9 | 96.5 |
| 1 l/ha CPA-2 + 0.5 l/ha ADJ-1 | 4.3 | 17.7 | 96.6 |
| 1 l/ha CPA-2 + 0.2 l/ha ADJ-2 | 6.3 | 16.5 | 92.7 |

The results demonstrate that the fungicide alone reduced the disease symptoms on both scoring dates and increased the grain yield over the untreated control. Both adjuvants tested improved the activity of the fungicide in winter wheat. Only the application of the fungicide together with the composition according to the invention resulted in a further yield increase. The success of the application of the composition according to the invention appears to be dose-independent.

Example 3.3: Winter Wheat

In a field with winter wheat cv. "Genius" at growth stage 49 (all leaves fully developed), the CPA-3 and the adjuvants ADJ-1 and ADJ-2 were diluted with 200 l/ha water and the mixture was sprayed onto the plants. Before the application, the plants were infected by *septoria* leaf spot (caused by the pathogenic fungus *Mycosphaerella graminicola*). The disease symptoms were determined 37 days after the application on the first leaf underneath the flag leaf and on the flag leaf. The application rates of the products and the results are shown in Table C.

TABLE C

Disease symptom of the leaves as per Example 3.3:

| Treatment | Disease symptoms, flag leaf [%] | Disease symptoms, leaf underneath flag leaf (%) |
|---|---|---|
| Untreated | 8.8 | 48.8 |
| 0.75 l/ha CPA-3 | 3.4 | 26.7 |
| 0.75 l/ha CPA-3 + 0.5 l/ha ADJ-1 | 3.3 | 20.3 |
| 0.75 l/ha CPA-3 + 0.2 l/ha ADJ-2 | 2.6 | 18.5 |

The results show that the fungicide alone reduced the disease symptoms on both leaves studied. Both test adjuvants improved the activity of the fungicide in winter wheat further, especially on the leaf underneath the flag leaf.

Example 3.4: Soybean

In a field with soybeans cv. "Potencia" at growth stage R3 (beginning pod), the CPA-4 and the adjuvants ADJ-1 and ADJ-2 were diluted with 150 l/ha water and the mixture was sprayed onto the plants. Before the application, the plants were infected by rust disease (caused by the pathogenic fungus *Phakopsora pachyrhizi*). The disease symptoms were determined 14 and 28 days after the application, on the lower leaves of the plants. The application rates of the agents and the results are shown in Table D.

TABLE D

Disease symptoms of the leaves and grain yield as per Example 3.4:

| Treatment | Disease symptoms, 14 days [%] | Disease symptoms, 28 days (%) |
|---|---|---|
| Untreated | 11.7 | 42.7 |
| 0.1 l/ha CPA-4 | 8.4 | 34.1 |
| 0.1 l/ha CPA-4 + 0.2 l/ha ADJ-1 | 4.9 | 20.3 |
| 0.1 l/ha CPA-4 + 0.4 l/ha ADJ-1 | 4.5 | 16.0 |
| 0.1 l/ha CPA-4 + 0.2 l/ha ADJ-2 | 4.6 | 22.1 |

The results show that the fungicide alone reduced the disease symptoms on the soybean plants in comparison with the untreated control. Both test activity adjuvants improved the efficacy of the fungicide.

Example 3.5: Cotton

In a field with cotton plants cv. "Fiber Max" at beginning of anthesis (flowers unopened, plants are approximately 70 cm in height), the CPA-5 and the adjuvants ADJ-1 and ADJ-2 were diluted with 150 l/ha water and the mixture was sprayed onto the plants. After the spray coating had dried on (approximately 1 hour after the application), half of the treated plots were sprayed from a nozzle with approximately 8 mm/m² water so as to simulate rain. The purpose was to determine whether the rain simulation washed off the crop protection agent and whether this would result in a reduced activity against the insects. The number of aphids (Aphidae) was counted on 10 leaves per plot 7 days after the application and is shown in Table E and the application rates of the agents are stated.

TABLE E

Number of aphids per leaf as per Example 3.5, in parentheses % of untreated:

| Treatment | Without rain | After rain simulation |
|---|---|---|
| Untreated | 18.8 (100) | 13.1 (100) |
| 0.1 kg/ha CPA-5 | 10.7 (57) | 9.8 (75) |
| 0.1 kg/ha CPA-5 + 0.2 l/ha ADJ-1 | 9.1 (48) | 7.5 (57) |
| 0.1 kg/ha CPA-5 + 0.4 l/ha ADJ-1 | 7.2 (38) | 6.5 (50) |
| 0.1 kg/ha CPA-5 + 0.2 l/ha ADJ-2 | 9.8 (52) | 7.1 (54) |

The results demonstrate that the application of the insecticide alone reduced the number of aphids. Obviously, some of the insecticide was washed off by rain unless combined with an adjuvant. Both adjuvants increased the activity of the insecticide, in particular the ADJ-1 at the higher dosage. In relative terms, the ADJ-1 increased the rainfastness of the insecticide to a similar extent as the commercial ADJ-2.

Example 3.6: Weeds in Crops

In a field with maize at growth stage 16 (6 leaves developed), cv. "Falkone", in plots in which the grass weed *Echinochloa crus-galli* (approx. 10 plants per m², with 2-3 leaves per plant) and also the broad-leaved weed *Chenopodium album* (approx. 10 plants/m², likewise with 2-3 leaves) occurred, the CPA-6 alone or together with the adjuvants ADJ-1 or ADJ-2 was diluted with 200 l/ha water and the mixture was sprayed onto the plants. The CPA-6 consists of two components, rimsulfuron, which preferentially inhibits the growth of grasses, and dicamba, which controls broad-leaved weeds. Both agents are selective in maize, which means that the herbicide does not damage maize. The occurrence of two target weeds was scored 52 days after the plants had been sprayed, and the activity of the treatment was scored in relation to the plants' growth in the untreated control. The degree of weed cover of the control area was 32%, and the degree of cover of the treatment area was 39%. The data in Table F express the efficacy of the treatment. The application rates of the agents and the results are shown in Table F.

TABLE F

Efficacies (%) of the treatment on the grass *Echinochloa crus-galli* and the broad-leaved weed *Chenopodium album* as per Example 3.6:

| Treatment | Efficacy against grass [%] | Efficacy against broad-leaved weeds [%] |
|---|---|---|
| CPA-6 (0.025 kg Cato + 0.25 l Banvel 4S)/ha, | 55 | 65 |
| CPA-6 (0.025 kg Cato + 0.25 l Banvel 4S)/ha) + 0.25 l/ha ADJ-1 | 94 | 95 |

TABLE F-continued

Efficacies (%) of the treatment on the grass *Echinochloa crus-galli* and the broad-leaved weed *Chenopodium album* as per Example 3.6:

| Treatment | Efficacy against grass [%] | Efficacy against broad-leaved weeds [%] |
|---|---|---|
| CPA-6 (0.025 kg Cato + 0.25 l Banvel 4S)/ha) + 0.5 l/ha ADJ-1 | 97 | 94 |
| CPA-6 (0.025 kg Cato + 0.25 l Banvel 4S)/ha) + 0.2 l/ha ADJ-2 | 91 | 94 |

The results show that both adjuvants increase the efficacies of the herbicide combination to above 90%, while the herbicides alone only exerted a weak activity. The activity of the composition according to the invention appears to be dose-independent.

Example 3.7: Weed without Crop, Nonselective Herbicide

*B. decumbens* and *G. horizontalis* and also *A. hispidum* were sown in a field. When the plants had reached a growth height of 30-35 cm (*B. decumbens*) and 35-40 cm (*D. horizontalis*) and 50-60 cm (*A. hispidum*) respectively, they were treated with CPA-7 alone or in diluted form together with adjuvants ADJ-1 or ADJ-2 with 150 l/ha of water. The CPA-7, as is known, is not very rainfast, i.e. if rain falls shortly after the application, the activity is greatly reduced because agents are washed off the plants by the rain. To improve the rainfastness, one may resort to adjuvants. For this reason, the plots were designed in duplicate (with the respective 4 replications), and 1 hour after the application 8 mm/m² of water was sprayed over a period of 10 minutes, using a nozzle, so as to simulate rain. The activity of the applications was scored 30 days after the application. The data in Table G show the degree of efficacy of the treatment. The application rates of the agents and the results are shown in Table G.

TABLE G

Degrees of efficacy (%) of the treatment on the grasses *Brachiaria decumbens* (a) and *Digitaria horizontalis* (b), and on the broad-leaved plant *Acanthospermum hispidum* (c), without rain and after simulated rain post-application as per Example 3.7.

| | Treatment | Efficacy without rain [%] | Efficacy after rain (simulated) [%] |
|---|---|---|---|
| (a) | 0.75 l/ha CPA-7 | 79 | 61 |
| | 0.75 l/ha CPA-7 + 0.2 l/ha ADJ-1 | 89 | 74 |
| | 0.75 l/ha CPA-7 + 0.4 l/ha ADJ-1 | 96 | 79 |
| | 0.75 l/ha CPA-7 + 0.2 l/ha ADJ-2 | 85 | 70 |
| (b) | 0.75 l/ha CPA-7 | 89 | 74 |
| | 0.75 l/ha CPA-7 + 0.2 l/ha ADJ-1 | 94 | 81 |
| | 0.75 l/ha CPA-7 + 0.4 l/ha ADJ-1 | 98 | 84 |
| | 0.75 l/ha CPA-7 + 0.2 l/ha ADJ-2 | 95 | 73 |
| (c) | 0.75 l/ha CPA-7 | 81 | 80 |
| | 0.75 l/ha CPA-7 + 0.2 l/ha ADJ-1 | 98 | 89 |
| | 0.75 l/ha CPA-7 + 0.4 l/ha ADJ-1 | 100 | 94 |
| | 0.75 l/ha CPA-7 + 0.2 l/ha ADJ-2 | 96 | 76 |

The results show that both adjuvants increased the efficacies of the nonselective herbicide. The composition according to the invention increased the activity of the nonselective herbicide after rain better than the commercial ADJ-2, in particular at the higher application rate.

The invention claimed is:

1. A self-emulsifying composition, comprising:
   at least one hydrophobic, at least partially water-insoluble polyglycerol ester in combination with at least one emulsifier,
   wherein the at least one hydrophobic, at least partially water-insoluble polyglycerol ester has an HLB value of 8 or less and is of Formula 2:

$$M_a D_b T_c \quad \text{Formula 2}$$

wherein
   $M=[C_3H_5(OR)_2O_{1/2}]$,
   $D=[C_3H_5(OR)_1O_{2/2}]$,
   $T=[C_3H_5O_{3/2}]$,
   a=1 to 10,
   b=0 to 10,
   c=0 to 3,
   wherein the sum total of a+b+c is 1 to 20,
   wherein the radicals R independently of one another are identical or different radicals of the formula R'—C(O)— or H,
   wherein R' is a monovalent aliphatic, saturated or unsaturated hydrocarbon radical having 3 to 39 C atoms,
   wherein at least one radical R corresponds to a radical of the formula R'—C(O)—, and
   wherein the acyl radicals are fatty acid mixtures comprising at least 70% by weight of oleic acid.

2. The composition of claim 1, wherein the at least one hydrophobic, at least partially water-insoluble polyglycerol ester has an HLB of from 4 to 6.5 and an arithmetic mean of 2.9 to 3.1 radicals R of the formula R'—C(O)—.

3. The self-emulsifying composition of claim 1, comprising an emulsifier with an HLB of 9 or greater.

4. The self-emulsifying composition of claim 3, comprising at least one sorbitan fatty acid ester as emulsifier.

5. An additive for a crop protection formulation, comprising the self-emulsifying composition of claim 1.

6. A method for avoiding spray drift, the method comprising adding the additive of claim 5 to a crop protection formulation.

7. A method for enhancing the efficacy of a pesticide and simultaneously for avoiding spray drift, the method comprising adding the additive of claim 5 to a crop protection formulation.

8. A method for enhancing the efficacy of a pesticide, simultaneously for avoiding spray drift and for increasing the yield of an agricultural crop, the method comprising adding the additive of claim 5 to a crop protection formulation.

9. The self-emulsifying composition of claim 1, wherein the at least one hydrophobic, at least partially water-insoluble polyglycerol ester is triglycerine trioleate.

10. The self-emulsifying compositions of claim 1, wherein the sum total of a+b+c is 2 to 5.

11. A spray mixture, comprising water and from 0.001 to 1 v % of the self-emulsifying composition of claim 1.

12. The spray mixture of claim 11, comprising 0.01 to 0.5 v % of the self-emulsifying composition.

13. The spray mixture of claim 11, comprising 0.02 to 0.15 v % of the self-emulsifying composition.

14. The spray mixture of claim 11, wherein, when the spray mixture is sprayed to produce a spray using a flat-spray nozzle of the type XR 11003 from TeeJet at a pressure of 1 bar and a temperature of 25° C., a volume fraction of droplets with a droplet diameter of less than 150 µm in the spray is 10% less than a volume fraction of droplets with a droplet diameter of less than 150 µm in a spray that is produced identically and is identical other than comprising none of the anti-adrift additive.

15. The spray mixture of claim 11, wherein, when the spray mixture is sprayed to produce a spray using a flat-spray nozzle of the type XR 11003 from TeeJet at a pressure of 1 bar and a temperature of 25° C., a maximum of the droplet size distribution of the spray is at least 5% more than a maximum of the droplet size distribution of a spray that is produced identically and is identical other than comprising none of the anti-adrift additive.

16. The spray mixture of claim 11, wherein, when the spray mixture is sprayed to produce a spray using a flat-spray nozzle of the type XR 11003 from TeeJet at a pressure of 1 bar and a temperature of 25° C., a volume-related median of the droplet size distribution of the spray is at least 5% more than a volume-related median of the droplet size distribution of a spray that is produced identically and is identical other than comprising none of the anti-adrift additive.

17. The spray mixture of claim 11, wherein, when the spray mixture is sprayed to produce a spray using a flat-spray nozzle of the type XR 11003 from TeeJet at a pressure of 1 bar and a temperature of 25° C., a volume-related median of the droplet size distribution of the spray is at least 5% more than a volume-related median of the droplet size distribution of a spray that is produced identically and is based on fully-demineralized water.

* * * * *